United States Patent [19]

Juge et al.

[11] Patent Number: 5,324,850
[45] Date of Patent: Jun. 28, 1994

[54] PREPARATION OF CHIRAL CATALYSTS BASED ON RUTHENIUM AND PHOSPHORUS COMPLEXES

[75] Inventors: Sylvain Juge, Orsay; Jean-Pierre Genet, Fontenay-aux-Roses; Sergio Mallart, Orsay, all of France

[73] Assignee: Societe Nationale Elf Aquitaine, France

[21] Appl. No.: 835,995

[22] PCT Filed: Aug. 10, 1990

[86] PCT No.: PCT/FR90/00607
§ 371 Date: Feb. 21, 1992
§ 102(e) Date: Feb. 21, 1992

[87] PCT Pub. No.: WO91/02588
PCT Pub. Date: Mar. 7, 1991

[30] Foreign Application Priority Data

Aug. 23, 1989 [FR] France .................. 8911159

[51] Int. Cl.$^5$ ............................. C07F 15/00
[52] U.S. Cl. ........................ 556/21; 556/136
[58] Field of Search .................. 556/21, 136

[56] References Cited

U.S. PATENT DOCUMENTS 5,021,593  6/1991  Nohira et al. .................. 556/20
5,118,825  6/1992  Wu .................................. 556/21

OTHER PUBLICATIONS

Ikariya et al., J. Chem. Soc., Chem. Commun., pp. 922-924 (1985).
Stephenson et al., J. Inorg. Nucl. Chem., vol. 28, pp. 945-956 (1966).
Noyori et al., J. Am. Chem. Soc., vol. 109, No. 19, pp. 5856-5858 (1987).
Kitamura et al., J. Am. Chem. Soc., vol. 110, No. 2, pp. 629-631 (1988).

*Primary Examiner*—José G. Dees
*Assistant Examiner*—Porforio Nazario
*Attorney, Agent, or Firm*—Ostrolenk, Faber, Gerb & Soffen

[57] ABSTRACT

Method for the preparation of a chiral catalyst, comprised of an organic complex of ruthenium and phosphorus, consisting in heating a complex of ruthenium with a phosphine, within an organic liquid, inert in relation to substances in presence, the heated complex being based on a diene and an allylic compound; the product obtained following the heating is subjected to the action of an acid in an organic solvent.

17 Claims, No Drawings

PREPARATION OF CHIRAL CATALYSTS BASED ON RUTHENIUM AND PHOSPHORUS COMPLEXES

The invention relates to the preparation of optically active catalysts formed by ruthenium complexes in which the ligand is an organic phosphorus derivative. It relates in particular to asymmetric hydrogenation catalysts and double bond isomerization catalysts which make it possible to obtain organic products of desired chirality. The method according to the invention makes it possible to obtain products of improved optical purity in cases where the latter is inadequate when applying the catalysts obtained according to the prior art. The catalysts formed by the method according to the invention are very advantageously suitable for the preparation of amino acids, and particularly L-threonine, by hydrogenation of the corresponding ketones, and in general of compounds carrying a carbonyl and an amine or amide group.

At the present time, various phosphine complexes of Ru are known which are used as asymmetric hydrogenation catalysts. An example of such a complex is bis(2-methylallyl)bis(triphenylphosphine)Ru, which is described by J. POWELL and B. L. SHAW in Journ. Chem. Soc. n° A, 1968, pages 159–161. In the literature on this subject, the useful organophosphorus ligands are denoted by abbreviations such as DIOP, DIPAMP, CHIRAPHOS, BINAP etc., which are generally phosphines such as, for example,

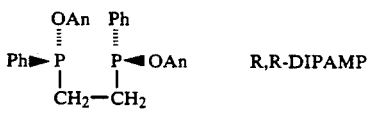   R,R-DIPAMP i.e. 1,2-bis(o-anisylphenylphosphino)ethane, wherein OAn is o-anisyl. In general, these ligands are combined with a halide or an organic compound of Ru, especially a carboxyl or unsaturated group and in particular an allyl group.

Thus R. NOYORI et al.—J. Amer. Chem. Soc. 1987, 109, pages 5856–5858—have described the asymmetric hydrogenation of several carboxylic acid esters carrying a ketone group in the β position, converting said group to a hydroxyl according to the equation

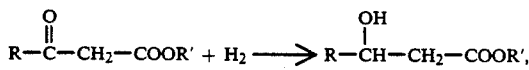

the catalyst being RuX$_2$[(R or S)-BINAP], where BINAP denotes the diphosphine

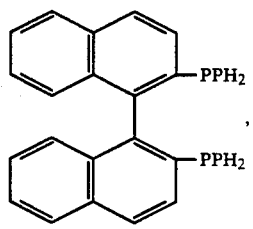

X being Cl, Br or I.

Depending on the R or S configuration of this ligand, the authors obtained the β-hydroxyester mainly in one or other of these configurations, the enantiomeric purity always being very high.

Likewise, M. KITAMURA et al., in J. Am. Chem. Soc. 1988, 110, pages 629–631, have reported similar asymmetric hydrogenations, with the same catalyst, carried out on substances in which the —CH$_2$—COOR' in the formula given above is replaced with —CH$_2$—N(R')$_2$, CH$_2$—OH, CH$_2$—CH$_2$OH, CH$_2$—COSR', —CH$_2$—COR', —CH$_3$CO, —C$_6$H$_4$— COOH, CH$_3$, —CO—CH$_3$, —CH$_2$—COR' or

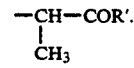

In these cases too, the yields of the hydrogenation are in general very high, as is the optical purity (% enantiomeric excess, e.e.).

However, it is found that if an attempt is made to carry out the same reactions with catalysts in which the BINAP group is replaced with a more economic group, for example one of those referred to above, the results become random and less satisfactory. The work from which the present invention is derived suggests that this disadvantage is due to the degradation undergone by the products during the preparation of the catalyst, which comprises heating a ruthenium compound with a phosphine. In fact, the article by TETSUO OHTA et al., Inorg. Chem. 1988, 27, page 567, or that by Takao IKARIYA et al., J. Chem. Soc., Chem. Commun. 1985, page 922, states that to prepare complexes of Ru with BINAP, a ruthenium compound is heated with the phosphine BINAP in toluene, in the presence of triethylamine, under reflux, i.e. at about 100° C., for 12 hours. Although the tetraphenyldinaphthyldiphosphine, i.e. the BINAP, and its reaction product withstand this treatment well, the same does not apply to the various other phosphines, which are more delicate. The interest of the present invention lies in the fact that very active catalysts based on complexes of Ru with phosphine ligands, which are more economic than those in the articles cited above, can be prepared industrially under milder conditions by a novel improved method.

In the method according to the invention, a complex of ruthenium with both a diene and an allyl compound is heated with a phosphine in an organic liquid which is inert towards the substances present, so as to replace the diene with the phosphine in the ruthenium complex; in this method, the product obtained is subjected to the action of an acid in an organic solvent.

Various mineral or organic acids are suitable for carrying out the method, examples being hydracids, sulfuric acid, sulfonic acids, perchloric acid, phosphorus acids, fluorosulfonic acid, acetic acid, propionic acids, benzoic acid and the like. It is particularly practical to use hydracids, especially HCl, HBr, HI or HBF$_4$ and in particular HBr.

According to a preferred procedure, the allyl complex of Ru-phosphine is dissolved in an appropriate organic solvent and the solution is stirred with the acid diluted beforehand in an organic liquid which is the same as or different from said solvent.

It is advisable to use the solution of the acid at a concentration of 0.2 to 3N, and preferably of 0.5 to 1.5N, the amount of acid being at least 2 equivalents, preferably 2 to 4 equivalents, per Ru atom present.

The solution of complex, stirred with the acid in this way, is preferably kept at a temperature of 0° to 40° C., room temperature, especially from 15° to 25° C., being entirely favorable. This treatment is continued until the allyl compound has been removed and replaced, in the complex, with the anion of the acid used. Depending on the nature of the substances present, the nature of the acid, the concentration of the latter and the temperature, the acid treatment according to the invention generally lasts about ¼ hour to 6 hours and most often 1 to 3 hours.

The reaction produced by the acid treatment according to the invention can be represented by the following equation:

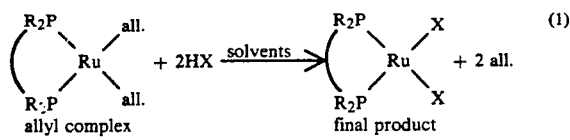

(all. denoting the allyl compound).

The preparation of a complex of ruthenium with a diene, the allylation of this complex and its reaction with a phosphine to give the starting material for operation (1) above are known in the art, so there is no need to describe them here. It will simply be pointed out that the Ru-diene complex can be obtained by reacting an Ru salt, for example $RuCl_3$, with a $C_4$ to $C_{16}$ diene which is preferably cyclic, such as cyclohexadiene, cycloheptadiene, cyclooctadiene, paramenthadiene, α-phellandiene, norbornadiene etc.

The allylation, which is also known per se, can be effected using various organometallic allyl compounds:

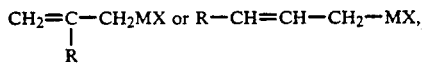

in which M is a metal, generally Mg, X is a halogen and R is an H atom or a hydrocarbon group, most often $C_1$ to $C_6$; as the allyl is removed in the final operation, according to the invention, it is advantageous to employ the least expensive compound; in practice, therefore, the allyl group (R=H) or methallyl group (R=$C_3$) is generally used.

The replacement of the diene with a phosphine ligand in the allyl complex is carried out broadly as in the prior art, except that the heating is effected at a lower temperature and for a shorter time. Thus an advantageous feature of the method of the invention is the fact that the phosphine allyl complex subjected to the acid treatment has been prepared by heating the diene-Ru-allyl complex with a phosphine at a temperature not exceeding 80° C. and preferably of between 60° C. and 80° C. Furthermore, this heating is not continued beyond 6 hours, the preferred time being 3 to 5 hours.

It is seen that the operating conditions are much less harsh than in the prior art (article by TETSUO OHTA cited above), where heating takes place for 12 hours at well above 80° C.

By way of a non-limiting example, a sequence of operations carried out to give a complex catalyst according to the invention is described below.

I—Formation of a Cyclooctadiene-$RuCl_2$ Complex

The reaction of $RuCl_3$ with the diene can be written as follows:

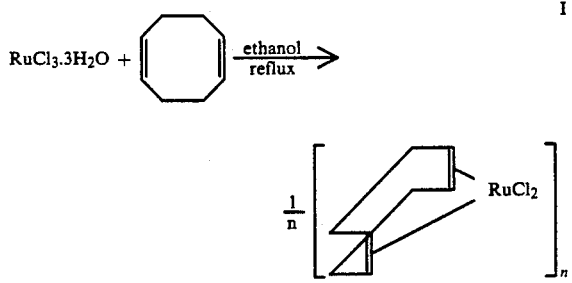

in which n is the degree of polymerization of the complex.

2.45 g of $RuCl_3.3H_2O$ are dissolved in 80 g of ethanol, and 8 g of cyclooctadiene are added. The medium is refluxed for 3 days; the solution obtained is filtered to leave 2.6 g of a brown solid, which is the 100% pure cyclooctadiene-$RuCl_2$ complex.

II—Allylation of the Cyclooctadiene-$RuCl_2$ Complex

The complex obtained in I is reacted with the methallyl magnesium compound

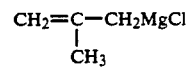

in ether to give

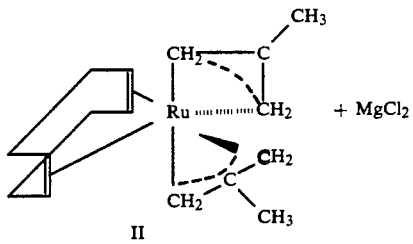

To do this, the 2.6 g (9.3 mmol) of complex obtained above are placed in 150 ml of ether and mixed with 120 ml of a suspension of 48 mmol of methallyl magnesium chloride in ether, i.e. a 0.4M suspension of magnesium compound.

There are 5.16 mol of magnesium compound per mol of cyclooctadiene-Ru complex.

The mixture is stirred for 6 hours at 20° C. and then filtered on "Celite". In the filtrate, cooled to 0° C., the excess methallyl magnesium compound is hydrolyzed with 100 ml of iced water.

The aqueous phase is decanted and treated with three times 100 ml of ether in order to extract the allyl complex II formed. The organic phases are combined, dried over $CaCl_2$, filtered and concentrated. The residue is taken up with 9 ml of benzene and the solution obtained is passed through an alumina column; elution with 150 ml of benzene and evaporation of this solvent gives 2.7 g of a white solid containing 97% of the allyl complex II.

III—Phosphination

The diene is replaced in the complex II with a phosphine:

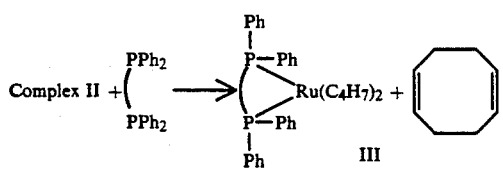

The reaction takes place in a Schlenck apparatus into which 200 mg of cyclohexadiene-Ru-bis(methallyl), obtained in the previous step, and 3 ml of hexane or toluene/hexane, degassed with a stream of argon, are introduced. After this, the desired diphosphine is added at a rate of 1 mol per Ru atom present. The solution is kept at a temperature of 60° to 80° C. for 3 to 5 hours. The complex formed then precipitates in hexane. After cooling, the supernatant solvent is drawn off with a syringe. The remainder is removed with a vane pump and the solid product formed is collected.

This procedure was applied to the ligands known by the following names: Diop, Binap, Univerphos, Norphos, Prophos, Deguphos, Dipamp, Bnpe, Dimpc and Bppm.

IV—Acid Treatment

The purpose of this additional operation according to the invention is to replace the allyl groups on the ruthenium with anions, as indicated above in the context of reaction (1).

In the specific non-limiting example in which the anions of the acid are Cl, the solid product resulting from operation III above was dissolved in 50 ml of dry degassed methylene chloride. 37 ml of an N solution of HCl in methanol, i.e. 37 mmol of HCl per 9 mmol of complex III present, were added to this solution. The mixture is stirred for 2 hours at room temperature and the solvent is then evaporated off to leave a reddish brown solid, which can be used directly as a catalyst.

In another example, in which the counterion is acetate ($CH_3CO_2-$), 50 mg of the solid product resulting from operation III above were dissolved in 2 ml of anhydrous degassed toluene. 2 equivalents, per Ru atom, of acetic acid dissolved in toluene (2M) were added to this solution. The mixture is stirred for 2 hours at room temperature and the solvent is then evaporated off under vacuum to give a solid, which can be used directly as a C=C reduction catalyst. Diop-Ru-$(OAc)_2$, Dipamp-Ru$(OAc)_2$ and Univerphos-Ru$(OAc)_2$, for example, were prepared in this way.

Using different phosphines, a series of several catalysts was prepared by the method according to the invention. Corresponding catalysts according to the prior art were also synthesized with the same phosphines, especially by reacting a diphosphine with a diene-RuCl$_2$ complex, as indicated by TETSUO OHTA in the article referred to above.

To estimate the value of the catalysts, they were tested in the asymmetric hydrogenation of methyl 3-aceto-2-acetamidobutyrate to produce methyl 3-hydroxy-2-acetamidobutyrate, which is easily converted to threonine. By choosing the catalyst of appropriate chirality, L-threonine is obtained; this is particularly sought after for its utility as an animal feed adjuvant. The hydrogenation experiments, followed by two other treatments, comprised the following reactions:

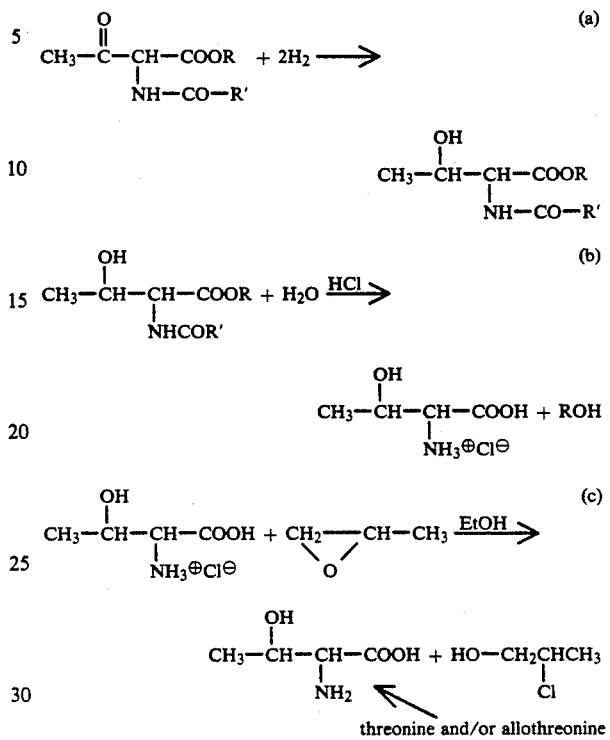

The experiments performed show that R and R', which are similar or different, can be a very wide variety of radicals, especially $C_1$ to $C_{12}$ alkyls and/or $C_6$ to $C_{10}$ aryls; as they are removed by reactions (b) and (c), they are preferably as economic as possible, i.e. most preferably $CH_3$ or $C_2H_5$ radicals.

To carry out the hydrogenation (a) in the absence of air, an autoclave was charged with 1 mmol of the aforementioned butyrate, 1 ml of a degassed solvent, generally THF, $CH_3OH$ or $C_2H_5OH$, and an amount of catalyst such that there was 1 Ru atom per 100 mol of butyrate. The autoclave was filled with hydrogen under 40 bar and evacuated at least 4 times, after which a hydrogen pressure of 90 bar was maintained for 48 hours. The solvent was then driven off under vacuum and the degree of conversion of —CO to —CHOH was determined by $^1H$ or $^{13}C$ NMR.

The hydrolysis (b) consisted in suspending the hydrogenated product in 3 ml of a 3N aqueous solution of HCl and refluxing this suspension for 3 hours. The liquid was then evaporated off under vacuum and the remaining solid was collected.

This was subjected to alcoholysis (c). For this purpose, it was taken up with 4 ml of ethanol and 2 ml of propylene oxide and refluxed for 15 minutes. After evaporation of the solvent, the product was taken up with 2 ml of acetone; a white powder was separated off by filtration of the acetone solution obtained.

The % by weight of threonine and the % enantiomeric excess of the L optical isomer of interest were determined on the product collected; the remainder generally consisted of allothreonine.

The results of these experiments are collated in the Table given below, which indicates the catalysts employed and the following data:

R-Cat.—yield of catalyst prepared by each of the 2 methods applied;

R-H—yield of the hydrogenation on the catalyst obtained by each of these methods;

Thr %—% by weight of threonine in the hydrogenated product;

e.e %—% enantiomeric excess of L-threonine.

The term "INVENTION" denotes the catalyst obtained by the novel method forming the subject of the present description, while "PRIOR ART" relates to the catalyst prepared in conventional manner, especially by the method according to TETSUO OHTA et al. cited above.

The following formulae and tradenames correspond to the catalysts shown in the Table of results on page 13.

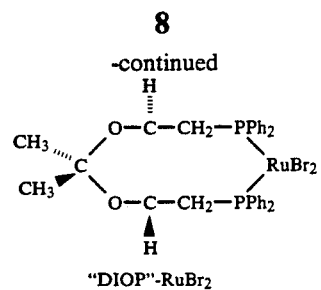

"DIOP"-RuBr$_2$

| Ex. n° | CATALYST | INVENTION | | | | PRIOR ART | | | |
|---|---|---|---|---|---|---|---|---|---|
| | | R-Cat. | R-H | Thr % | e.e. % | R-Cat. | R-H | Thr % | e.e. % |
| 1 | 1,2-bis(o-anisyl-phenylphosphino)-ethane-RuCl$_2$ "DIPAMP" | 76% | 80% | 88 | 30 | 27% | 80% | 80 | 0 |
| 2 | 1,2-bis(o-anisyl-phenylphosphino)-ethane-RuBr$_2$ "DIPAMP" | 81% | 90% | 80 | 32 | 29% | 80% | 79 | 0 |
| 3 | bis(diphenyl-phosphinobutane)-RuCl$_2$ "CHIRAPHOS" | 78% | 90% | 71 | 56 | 15% | — | — | — |
| 4 | bis(diphenyl-phosphinobutane)-RuBr$_2$ "CHIRAPHOS" | 82% | 91% | 95 | 74 | 17% | — | — | — |
| 5 | 2,3-0,0-isopropylidene-2,3-dihydroxy-1,4-bis(diphenylphosphino)butane-RuBr$_2$ "DIOP" | 76% | 89% | 70 | 53 | 12% | — | — | — |

EXAMPLE 1

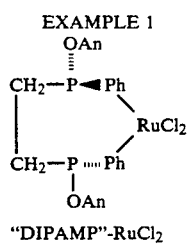

"DIPAMP"-RuCl$_2$

EXAMPLE 2
"DIPAMP"-RuBr$_2$

EXAMPLE 3

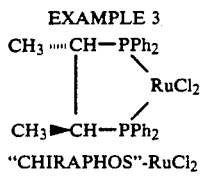

"CHIRAPHOS"-RuCl$_2$

EXAMPLE 4
"CHIRAPHOS"-RuBr$_2$

EXAMPLE 5

It is seen that the method of the invention makes it possible to obtain catalysts containing P and Ru, based on different phosphines, with good yields; these catalysts give very satisfactory hydrogenation results, it being possible for the products obtained to contain especially 70 to 95% of threonine and high proportions of L-threonine (e.e.=30 to 74%). By contrast, when applied to the same phosphines as the method of the invention, the known method (TETSUO OHTA cited above) gives the catalyst with poor yields; the impurity of the resulting products is such that—in certain cases (Examples 2 to 5)—it is not even possible to carry out the hydrogenation correctly, which explains the lack of data in the Table on the previous page. In Examples 1 and 2, where it was nevertheless possible to use the catalyst prepared in conventional manner, no enrichment of the L optical isomer of threonine is obtained (e.e.=0), in contrast to the enrichment obtained according to the invention.

What is claimed is:

1. A method of preparing a chiral catalyst consisting of an organic complex of ruthenium and phosphorus, which comprises heating a complex of ruthenium with a phosphine in an organic liquid which is inert towards the substances present, the heated complex being based on a diene and an allyl compound, wherein the product obtained after this heating is subjected to the action of an acid in an organic solvent.

2. A method according to claim 1 wherein the acid is a mineral or organic acid.

3. A method according to claim 2 wherein the acid is HCl, HBr, HI or HBF.

4. A method according to claim 1 wherein the solution of the acid in its solvent is 0.2 to 3N in request of the acid.

5. A method according to claim 1 wherein the amount of acid employed is at least 2 equivalents per Ru atom present.

6. A method according to claim 1 wherein the acid treatment takes place at a temperature of 0° to 40° C. for ¼ hour to 6 hours.

7. A method according to claim 1 wherein the product subjected to the acid treatment is produced by heating with the phosphine at a temperature not exceeding 80° C., the heating time not exceeding 6 hours.

8. A method according to claim 1 wherein the phosphine employed is a chiral diphosphine.

9. A method according to claim 2 wherein the acid is sulfuric, sulfonic, perchloric, phosphoric, fluorosulfonic, acetic, propionic or benzoic acid.

10. A method according to claim 4 in which the solution of the acid is 0.5 to 1.5N.

11. A method according to claim 5 wherein the amount of acid is 2 to 4 equivalents per Ru atom present.

12. A method according to claim 6 wherein the acid treatment takes place at a temperature between 15° and 25° C.

13. A method according to claim 7 in which the temperature is between 60° and 80° C. and the heating time is from 3 to 5 hours.

14. A method according to claim 16 wherein the acid is a hydroacid, sulfuric, sulfonic, perchloric, phosphoric, fluorosulfonic, acetic, propionic or benzoic acid; the solution is 0.5 to 1.5N and the amount of acid employed is 2 to 4 equivalents per Ru atom present.

15. A method according to claim 1 wherein the complex of ruthenium and the phosphine are such that the product of the process is an asymmetric hydrogenation catalyst.

16. In a method in which a compound carrying a carbonyl, amine or amide group is hydrogenated in the presence of a catalyst, the improvement which comprises utilizing as the catalyst, the chiral catalyst produced by the method of claim 1.

17. In a process in which an alkyl or aryl 3-aceto-2-amidobutyrate is hydrogenated in the presence of a catalyst in order to prepare threonine, the improvement which comprises utilizing as the catalyst, the chiral catalyst produced by the method of claim 1.

* * * * *